US007699786B2

(12) United States Patent
Takeoka et al.

(10) Patent No.: US 7,699,786 B2
(45) Date of Patent: Apr. 20, 2010

(54) ELECTRONIC BLOOD PRESSURE MONITOR (75) Inventors: Kohhei Takeoka, Kyoto (JP); Jim Jun Li, Winfield, IL (US); Shingo Yamashita, Kyoto (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 667 days.

(21) Appl. No.: 11/397,962

(22) Filed: Apr. 5, 2006

(65) Prior Publication Data

US 2007/0239040 A1    Oct. 11, 2007

(51) Int. Cl.
*A61B 5/02* (2006.01)

(52) U.S. Cl. .................. 600/485; 600/490; 600/500; 600/481

(58) Field of Classification Search ........... 600/480, 600/493, 485, 500, 495
See application file for complete search history.

(56) References Cited

U.S. PATENT DOCUMENTS

| | | | | | |
|---|---|---|---|---|---|
| 4,747,412 | A | * | 5/1988 | Yamaguchi | 600/496 |
| 5,058,601 | A | * | 10/1991 | Riker | 600/538 |
| 5,680,869 | A | * | 10/1997 | Ogura | 600/485 |
| 6,221,012 | B1 | * | 4/2001 | Maschke et al. | 600/301 |
| 6,327,495 | B1 | * | 12/2001 | Iwabuchi et al. | 600/547 |
| 6,648,828 | B2 | * | 11/2003 | Friedman et al. | 600/506 |
| 6,699,195 | B2 | * | 3/2004 | Nakazawa et al. | 600/485 |
| 2002/0184542 | A1 | * | 12/2002 | Vicard et al. | 713/300 |
| 2005/0096553 | A1 | * | 5/2005 | Nguyen | 600/495 |
| 2005/0187484 | A1 | * | 8/2005 | Sano et al. | 600/495 |
| 2006/0128360 | A1 | * | 6/2006 | Hibino | 455/411 |
| 2007/0100213 | A1 | * | 5/2007 | Dossas et al. | 600/300 |

FOREIGN PATENT DOCUMENTS

| | | |
|---|---|---|
| JP | 05-203161 | 8/1993 |
| JP | 05-334136 | 12/1993 |
| JP | 05-335992 | 12/1993 |
| JP | 3020497 | 1/1996 |
| JP | 2002-272686 | 9/2002 |
| JP | 2002-272687 | 9/2002 |
| JP | 2005-224440 | 8/2005 |

OTHER PUBLICATIONS

International Search Report dated Apr. 17, 2007, directed to counterpart PCT application PCT/JP2007/055701.

* cited by examiner

*Primary Examiner*—Robert L Nasser
*Assistant Examiner*—Michael D'Angelo
(74) *Attorney, Agent, or Firm*—Morrison & Foerster LLP (57) ABSTRACT

An electronic blood pressure monitor includes an activation controller for exerting control in response to a signal representative of an instruction received from a user to selectively activate a plurality of functions included in first and second function groups of the electronic blood pressure monitor. The first function group includes a measurement function provided by a blood pressure measurement unit and the second function group includes an information changing function associated with erasing a measured value or changing a set value. The activation controller includes a determining unit for determining whether the electronic blood pressure monitor is started by a specific function, and a setting unit driven by a decision made by the determining unit to set the second function group in an activatable state or an inactivatable state.

8 Claims, 8 Drawing Sheets

ELECTRONIC BLOOD PRESSURE MONITOR

BACKGROUND OF THE INVENTION

1. Field of the Invention

The present invention relates generally to electronic blood pressure monitors and particularly to electronic blood pressure monitors having a blood pressure measurement function as well as a function associated with erasing a measured value and/or changing a set value.

2. Description of the Background Art

Typically household electronic blood pressure monitors have a function storing measured blood pressure data and displaying a previously measured blood pressure value. If one is given such a blood pressure monitor he/she may desire to erase previous measurement data stored therein. Accordingly, conventionally there exists an electronic blood pressure monitor having a function erasing previous measurement data.

For example Japanese Patent Laying-Open No. 2005-224440 discloses a blood pressure monitor that can erase only a resultant measurement stored in memory that the user desires to erase. The user can erase only the others' measurement data.

Furthermore, there exists a blood pressure monitor having a function storing blood pressure data in association with date, time and other similar conditions for measurement and displaying a previous blood pressure value in association with such condition in the measurement. Such blood pressure monitor further has a function for example setting and changing before blood pressure measurement a value serving as a reference for a condition for measurement.

For example Japanese Patent Laying-Open Nos. 2002-272686 and 2002-272687 describe that a blood pressure monitor includes a switch operated to set and correct a time and a fast forward and reverse switch fast forwarding or reversing a time in setting and correcting it. The publications disclose that the switches can be operated to change date and time. If the blood pressure monitor has an incorrect date and time, the user can correct it. This can prevent a blood pressure value from being stored with an incorrect date and time (or a condition for measurement).

Allowing a user to freely erase measurement data and change a set value, as described above, however, can be inconvenient to a doctor or a similar supervisor of a subject. For example if the supervisor instructs the subject to measure blood pressure everyday, then, normally, the supervisor can obtain a resultant measurement in a subsequent day to for example see how the subject's blood pressure varies. However, if measurement data can be erased, as desired, and the subject is unsatisfied with the resultant measurement, the subject may erase the data of the resultant measurement, resulting in falsified measurement data.

Furthermore if the supervisor instructs the subject to measure blood pressure during a designated period of time the subject can change the set time to falsify the time of measurement.

SUMMARY OF THE INVENTION

The present invention has been made to overcome the above disadvantage and it contemplates an electronic blood pressure monitor that can prevent a subject from erasing a measured value and/or changing a set value.

The present invention in one aspect provides an electronic blood pressure monitor including a blood pressure measurement unit, a first storage, a first input device, and an activation controller. The blood pressure measurement unit measures blood pressure. The first storage stores resultant measurement information including data of the blood pressure measured by the blood pressure measurement unit. The first input device is operated by a user to input an instruction to selectively activate a plurality of functions included in a first function group and a second function group of the electronic blood pressure monitor. The first function group includes a measurement function provided by the blood pressure measurement unit. The second function group includes an information changing function associated with erasing a measured value or changing a set value. The activation controller exerts control in response to a signal representative of the instruction received via the first input device to selectively activate the plurality of functions. The activation controller includes a determining unit for determining whether the electronic blood pressure monitor is started by a specific operation, and a setting unit driven by a decision made by the determining unit for setting the second function group in an activatable state or an inactivatable state. If the signal corresponds to a the first function group or if the signal corresponds to the second function group and the setting unit also sets the second function group in the activatable state, the activation controller activates the function corresponding to the signal.

Preferably the electronic blood pressure monitor further includes a display and the first function group further includes a first display function displaying on the display the resultant measurement information stored in the first storage.

Preferably the resultant measurement information further includes condition specifying data associated with each blood pressure for specifying a condition while measuring the blood pressure and the information changing function includes at least one of an erasure function erasing the resultant measurement information stored in the first storage and a value changing function changing a value serving as a reference for the condition for measurement.

Preferably if the determining unit determines that the electronic blood pressure monitor is started by the specific operation the setting unit sets the second function group in the activatable state, and if the determining unit determines that the electronic blood pressure monitor is started by an operation other than the specific operation the setting unit sets the second function group in the inactivatable state.

Preferably the electronic blood pressure monitor further includes a timer for counting time and the condition specifying data includes data of time counted by the timer when the blood pressure monitor measures the blood pressure.

Preferably the electronic blood pressure monitor further includes a second storage for storing history information indicating that the electronic blood pressure monitor is started by the specific operation and the second function group further includes a second display function displaying on the display the history information stored in the second storage.

Preferably the electronic blood pressure monitor further includes a timer for counting date and time and the activation controller further includes a data storer for storing start date and time data as the history information to the second storage, as based on an output provided from the timer, when the determining unit determines that the electronic blood pressure monitor is started by the specific operation.

Alternatively the activation controller preferably further includes a counter for counting how many times the electronic blood pressure monitor is started by the specific operation when the determining unit determines that the electronic blood pressure monitor is started by the specific operation, and a data storer for storing data of how many times the electronic blood pressure monitor is started by the specific operation, as counted, as the history information to the second storage.

Preferably the specific operation is included in power-on operations to start the electronic blood pressure monitor and is other than an explicit normal one of the power-on operations.

Preferably the first input device includes a plurality of switches capable of being pressed by the user and the determining unit determines that the electronic blood pressure monitor is started by the specific operation when the user simultaneously presses at least two prescribed ones of the plurality of switches.

Alternatively the electronic blood pressure monitor may further includes a second input device hidden from external and the determining unit may determine that the electronic blood pressure monitor is started by the specific operation when the second input device is operated.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Configuration

Figure 1:
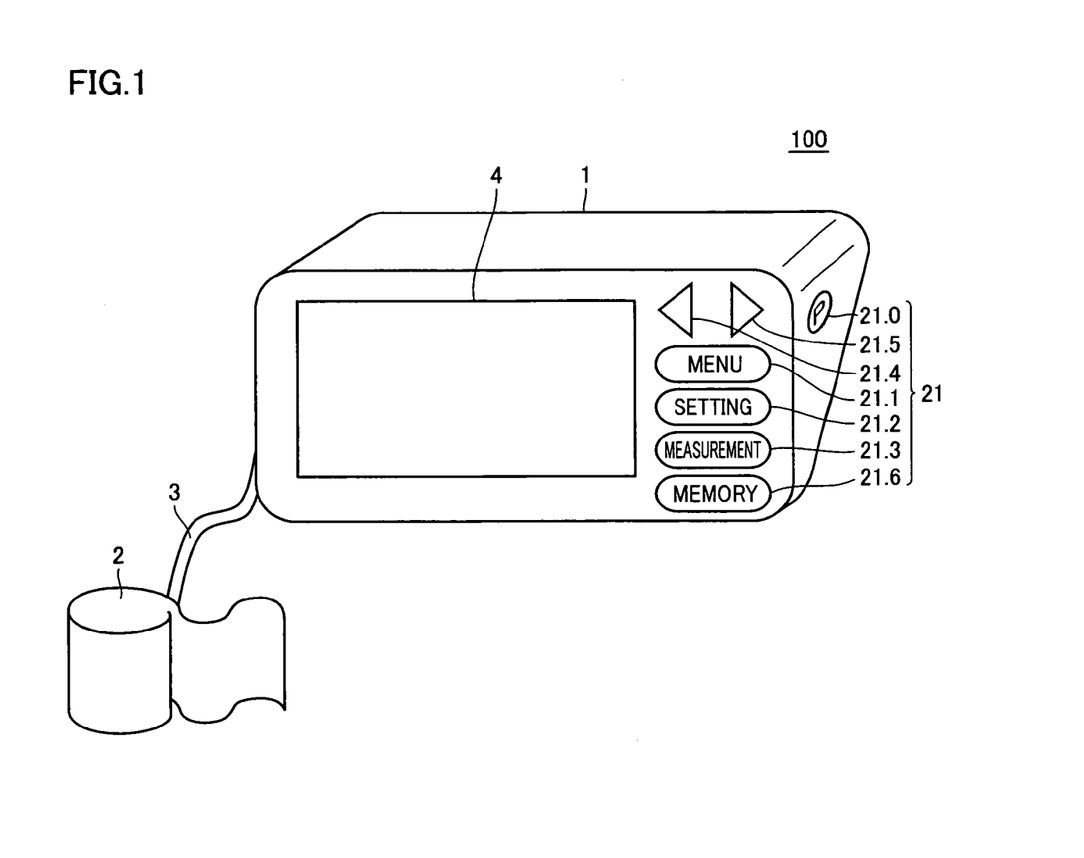
FIG. 1 generally shows an appearance of the present electronic blood pressure monitor in an embodiment and an exemplary variation thereof.

FIG. 1 generally shows an appearance of an electronic blood pressure monitor 100 in an embodiment of the present invention.

With reference to the figure the present embodiment provides electronic blood pressure monitor 100 including the blood pressure monitor's main body 1, a cuff 2 attached to a user's body at a prescribed site and receiving air pressure to pressurize the site, and an air tube 3 connecting main body 1 and cuff 2 together.

Main body 1 includes a display 4 allowing the user to confirm displayed information, and a console 21 operated by the user to input an instruction. Display 4 is for example a liquid crystal display (LCD). Console 21 includes a plurality of switches, e.g., a power supply switch 21.0, a menu switch 21.1, a setting switch 21.2, a measurement switch 21.3, a left switch 21.4, a right switch 21.5, and a memory switch 21.6. Power supply switch 21.0 is operated to input an instruction to turn on and off a power supply. Menu switch 21.1 is operated to display information of functions of electronic blood pressure monitor 100 in the form of a menu. Setting switch 21.2 is operated to effect a setting operation associated with information displayed on display 4. Measurement switch 21.3 is operated to start an operation to measure blood pressure. Left switch 21.4 and right switch 21.5 are operated to move leftward (or upward) and rightward (or downward), respectively, a cursor (not shown) displayed on display 4. Memory switch 21.6 is operated to input an instruction to display previous, resultant measurement information, which will be described later. Console 21 can receive an instruction issued from the user to selectively activate a plurality of functions included in first and second function groups that electronic blood pressure monitor 100 has. The first and second function groups will be described later.

Figure 2:
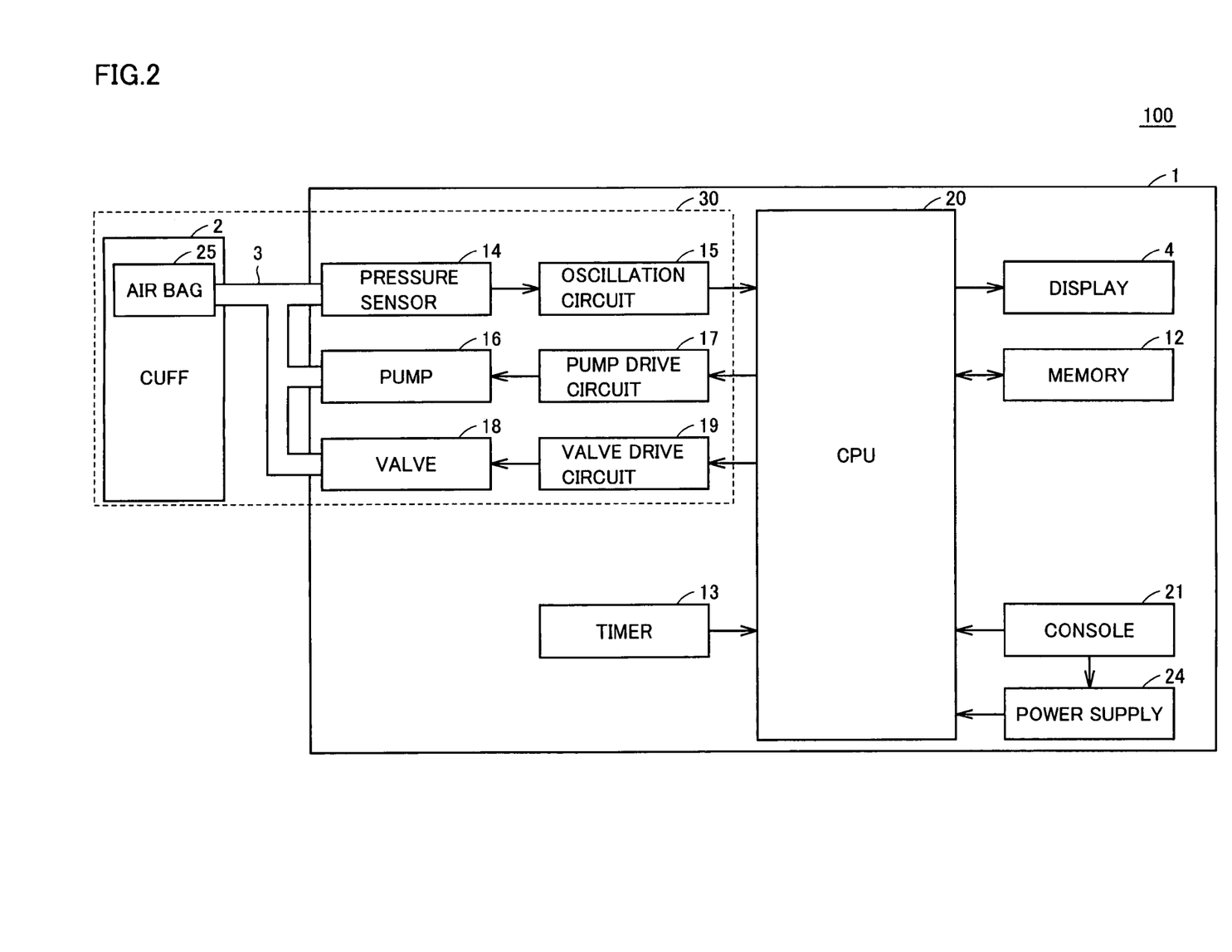
FIG. 2 is a block diagram showing a hardware configuration of the present electronic blood pressure monitor in an embodiment and an exemplary variation thereof.

FIG. 2 is a block diagram showing a hardware configuration of the present electronic blood pressure monitor 100. With reference to the figure, electronic blood pressure monitor 100 includes a blood pressure measurement unit 30 for measuring blood pressure, a CPU 20 intensively controlling and monitoring each component or the like, display 4, a memory 12 having a variety of data and programs stored therein, console 21, a timer 13 counting time to output data of counted time, and a power supply 24 supplying power. In the present embodiment blood pressure measurement unit 30 includes cuff 2, as described above, an air bag 25 incorporated in cuff 2, a pressure sensor 14 varying in capacity with the pressure internal to air bag 25 (hereinafter referred to as "cuff pressure"), an oscillation circuit 15 outputting to CPU 20 a signal of an oscillation frequency corresponding to a value in capacity of pressure sensor 14, a pump 16 and a valve 18 adjusting the cuff pressure in level, a pump drive circuit 17 driving pump 16, and a valve drive circuit 19 adjusting how valve 18 is opened and closed in degree. Air bag 25 and pressure sensor 14, and pump 16 and valve 18 are connected by air tube 3. Note that blood pressure measurement unit 30 is not limited such a configuration as described above, and may be of any configuration that can detect pulse wave information, i.e., information for measuring blood pressure. Furthermore, electronic blood pressure monitor 100 may also include a buzzer (not shown) generating an audible alarm.

Figure 3A:
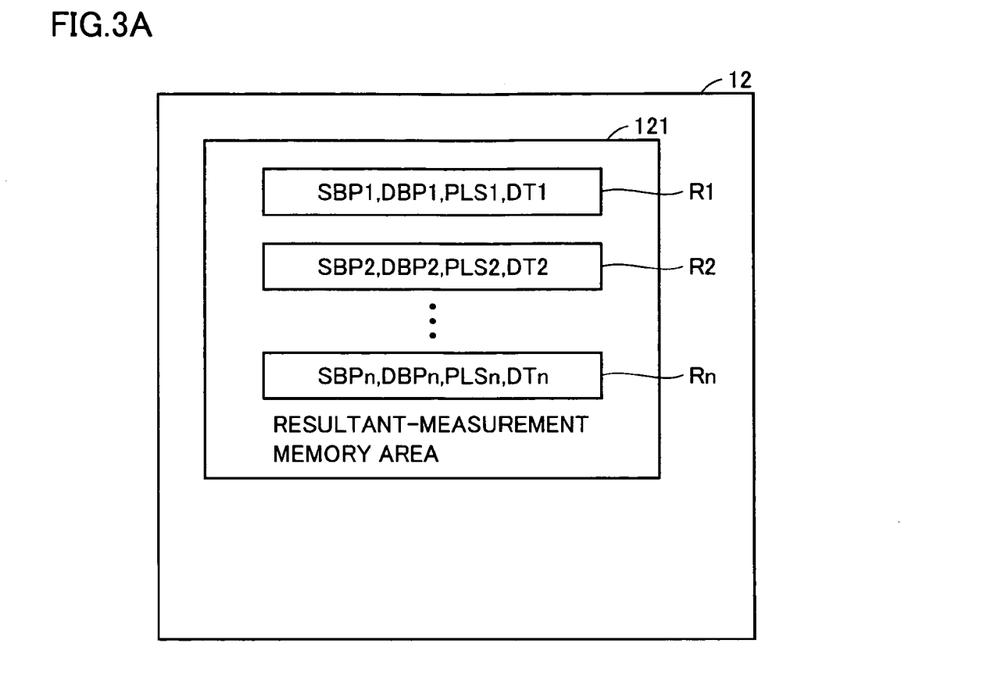
FIG. 3A shows an example in configuration of a memory in an embodiment of the present invention and FIG. 3B is a block diagram representing a function of a CPU in the present electronic blood pressure monitor in an embodiment.

In the present embodiment memory 12 has a configuration by way of example as shown in FIG. 3A. Memory 12 includes an area 121 for storing resultant measurement information.

With reference to FIG. 3A area 121 stores measured blood pressure data and condition data for specifying a condition in measuring blood pressure. Note that area 121 stores the measured blood pressure data and the condition data in a pair. As shown in FIG. 3A, a blood pressure value and a pulse rate are associated with a date and time of measurement (e.g., a date and time when measurement starts or ends) to form a record R which is stored for each blood pressure measurement. Record R stores systolic blood pressure data SBP, diastolic blood pressure data DBP, pulse rate data PLS, and measurement date and time data DT. Note that these data are not limited to a form of storage employing record R and may be stored in any form that allows the data to be associated for each measurement and stored at each area.

The present electronic blood pressure monitor 100 has two manners to start the same. One is a manner to do so by a normal operation (an operation explicitly starting the blood pressure monitor). The normal operation in the present embodiment corresponds to pressing (or operating) power supply switch 21.0. Power supply switch 21.0 preferably has a surface with an indication such as "power on/off". The other is a manner to start the electronic blood pressure monitor by an implicit, specific operation (an operation different from the normal operation explicitly starting the blood pressure monitor). The specific operation in the present embodiment corresponds for example to pressing (or operating) power supply switch 21.0, setting switch 21.2 and measurement switch 21.3 simultaneously.

In the present embodiment when the normal operation is performed to start electronic blood pressure monitor 100, electronic blood pressure monitor 100 operates in a lock mode, as will be described later. In contrast, if the implicit, specific operation is performed to start electronic blood pressure monitor 100, electronic blood pressure monitor 100 operates in an unlock mode described later. Accordingly, in the present embodiment, starting the electronic blood pressure monitor by the specific operation will also be referred to as "starting the electronic blood pressure monitor to operate in the unlock mode." (hereinafter referred to as "unlock start")

Figure 3B:
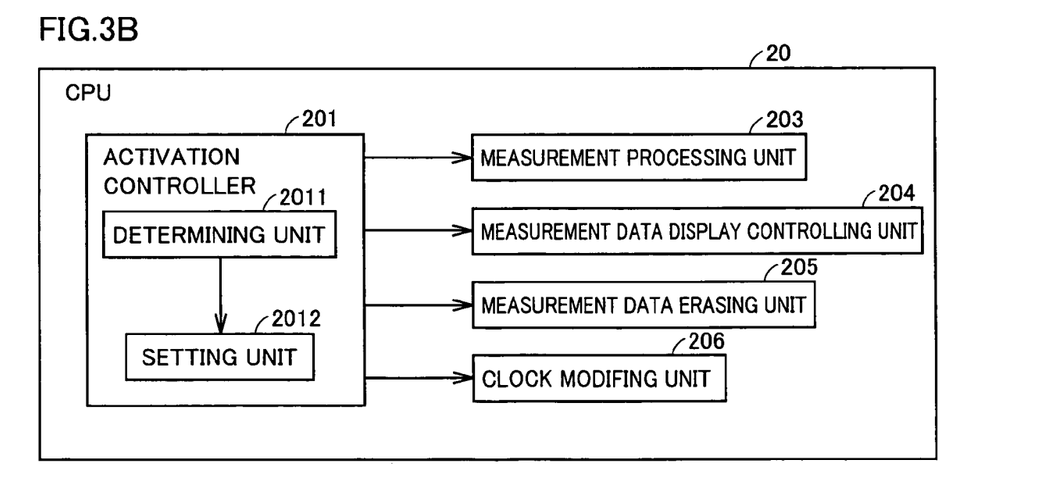

FIG. 3B is a block diagram representing a function of CPU 20 of the present electronic blood pressure monitor 100. CPU 20 includes an activation controller 201 operative in response to an instruction signal received via console 21 to exert control to selectively activate a plurality of functions of electronic blood pressure monitor 100. Activation controller 201 includes a determining unit 2011 determining whether the electronic blood pressure monitor is started by the specific operation, and a setting unit 2012 driven by a decision made by determining unit 2011 to set the second function group in an activatable or inactivatable state. Specifically, setting unit 2012 sets either the lock mode or the unlock mode. If the user inputs an instruction to activate a function included in the first function group, or if the user inputs an instruction to activate a function included in the second function group and setting unit 2012 also sets the second function group in the activatable state, activation controller 201 activates the function corresponding to the instruction.

The first and second function groups will now be described. The first function group at least includes a measurement function provided by blood pressure measurement unit 30 and in the present embodiment has the measurement function and in addition thereto a measurement data display function. Thus the first function group may be defined as a basic function group of electronic blood pressure monitor 100. In contrast, the second function group may be defined as an accompanying function group of electronic blood pressure monitor 100. The accompanying function group at least includes an information changing function associated with erasing a measured value and/or changing a set value. Specifically, this function includes at least one of an erasure function erasing at least one of a plurality of measurement data (or a pair of data of a measured value and a condition for measurement) stored in area 121, and a value changing function changing before blood pressure measurement a set value serving as a reference for a condition for measurement. In the present embodiment the information changing function includes both the erasure function and the value changing function.

Again with reference to FIG. 3B CPU 20 includes a measurement processing unit 203, a measurement data display controlling unit 204, a measurement data erasing unit 205, and a clock modifying unit 206 performing processes corresponding to the above described measurement function, measurement data display function, erasure function and value changing function, respectively. Each component performs a process, as will be more specifically described hereinafter. Note that these processes may be implemented by well-known techniques.

Measurement processing unit 203 controls driving of pump drive circuit 17 and valve drive circuit 19 and receives a signal from oscillation circuit 15 to convert the signal to a pressure signal to detect pressure. For the detected pressure data a prescribed algorithm is applied to calculate a blood pressure value or systolic blood pressure and diastolic blood pressure as well as a pulse rate. Such measurement procedure can be implemented by a conventionally provided, well-known procedure. Furthermore, measurement processing unit 203 obtains date and time of measurement, as based on date and time data provided from timer 13, and displays the calculated blood pressure value and pulse rate on display 4 and also stores the calculated blood pressure value and pulse rate associated with the date and time data as record R to area 121.

Measurement data display controlling unit 204 reads resultant measurement information stored in area 121 and performs a process to display it on display 4. More specifically, for example if memory switch 21.6 is initially pressed, measurement data display controlling unit 204 reads immediately previous measurement data and displays the data on display 4 and furthermore, whenever memory switch 21.6 being pressed is detected, measurement data display controlling unit 204 reads previous measurement data, one at a time, and displays the data.

Measurement data erasing unit 205 for example displays measurement data, one at a time, on display 4 and when a prescribed operation is performed (e.g., memory switch 21.6 and right switch 21.5 are simultaneously operated) measurement data erasing unit 205 erases currently displayed measurement data in units of record R. Note that measurement data erasing unit 205 may be adapted to erase all measurement data.

Clock modifying unit 206 performs a process to set a time in timer 13, and a process to change a set time (or value) in timer 13.

Thus if the user inputs an instruction to activate a function included in the basic function group, activation controller 201 can activate the function corresponding to the instruction, regardless of whichever one of the lock mode and the unlock mode may be set. In contrast, if the user inputs an instruction to activate a function included in the accompanying function group, then activation controller 201 can activate the function corresponding to the instruction only when setting unit 2012 sets the unlock mode. The operation of each functional block may be implemented by software stored in memory 12, or at least one of the operations may be implemented by hardware.

Note that while as described in the present embodiment, measurement is done under a condition determined with reference to a value (a set value) representing time (date and time) in electronic blood pressure monitor 100, it is not limited thereto. Measurement may be done under a condition determined with reference to a value (a set value) replacing date and time/representing date and time and in addition, e.g., how many times electronic blood pressure monitor 100 successively performs the blood pressure measurement process (i.e., a frequency of successive measurements), an interval of time applied in successively performing the blood pressure measurement process, a time to generate an audible alarm to issue a request to start measurement (i.e., an alarm time), and the like. In other words, as the process corresponding to the value changing function, CPU 20 may further perform a process to change a frequency of successive measurements, a process to change an interval of time, and/or a process to change an alarm time. If a condition for measurement includes a frequency of successive measurements, an interval of time, an alarm time and other similar items, each set value may be stored in memory 12 at a prescribed area. When blood pressure is measured, each set value may be associated with the measured blood pressure value and thus stored to memory 12 at area 121. Alternatively, if a set value corresponding to any condition/item for measurement is changed, the changed item's specifics (e.g., the item's name and value as changed) may be stored to memory 12 at an area (not shown) other than area 121 together with the date and time at which the set value is changed.

Figure 4:
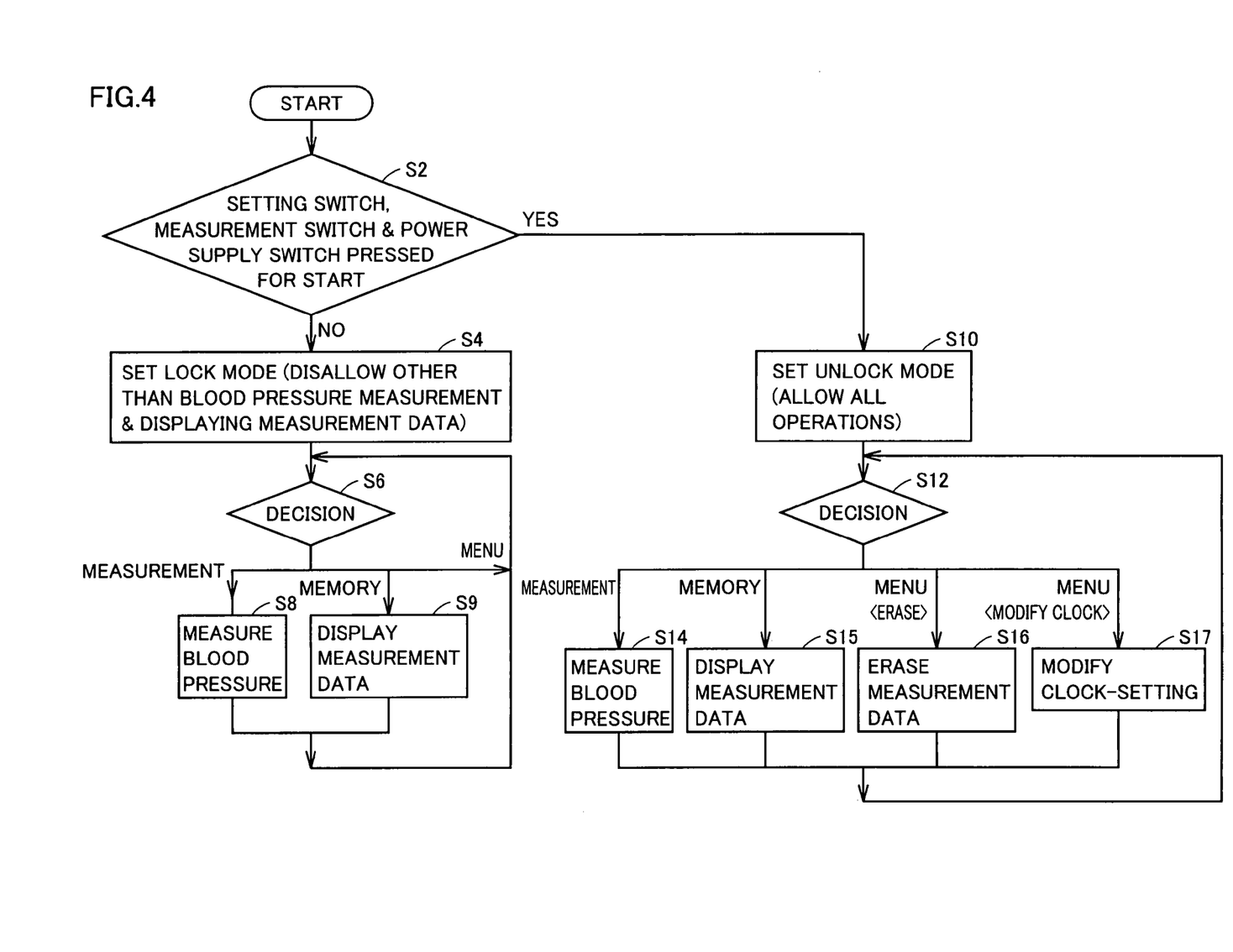
FIG. 4 is a flow chart of a process associated with measurement in an embodiment of the present invention.

FIG. 4 is a flow chart of a process associated with measurement in the present embodiment. The FIG. 4 flow chart shows a process previously stored in memory 12 as a program and implemented by CPU 20 reading and executing the program. The "process associated with measurement" is a process associated with blood pressure measurement and in the present embodiment includes processes performed by measurement processing unit 203, measurement data display controlling unit 204, measurement data erasing unit 205, and clock modifying unit 206, respectively.

Note that for the sake of illustration the FIG. 4 process is for example a process that is started when a user operates power supply switch 21.0 at least to supply power via power supply 24 to CPU 20 and that is performed when power supply is turned on. Furthermore for the sake of illustration memory 12 has also stored therein a power supply management program controlling how power supply is turned on. Upon power on, the power supply management program determines whether electronic blood pressure monitor 100 is started by the specific operation and a flag indicative of the decision is stored in an internal memory (not shown) for the sake of illustration.

With reference to FIG. 4, determining unit 2011 determines whether setting switch 21.2, measurement switch 21.3 and power supply switch 21.0 are simultaneously pressed to start electronic blood pressure monitor 100, i.e., whether the specific operation is performed to start electronic blood pressure monitor 100 (step S2). More specifically, this decision is made from a status of the flag set in the internal memory. If determining unit 2011 determines that electronic blood pressure monitor 100 is started by the normal operation (NO at step S2) the process proceeds to step S4. In contrast, if determining unit 2011 determines that electronic blood pressure monitor 100 is started by the specific operation (YES at step S2) the process proceeds to step S10.

At step S4, setting unit 2012 sets the lock mode. More specifically, setting unit 2012 sets the accompanying function group in the inactivatable state.

Subsequently activation controller 201 determines an instruction received from the user (step S6). More specifically it determines whether which switch of console 21 has been operated. If at step S6 a decision is made that measurement switch 21.3 has been pressed, measurement processing unit 203 performs the blood pressure measurement process (step S8). When step S8 completes, the process returns to step S6.

If at step S6 a decision is made that memory switch 21.6 has been pressed, measurement data display controlling unit 204 performs a process to display resultant measurement information on display 4 (step S9). When step S9 completes, the process returns to step S6.

If at step S6 a decision is made that menu switch 21.2 has been pressed, activation controller 201 waits.

Thus in the lock mode while an operation of a switch that is performed to activate a function included in basic function group is validated an operation of a switch (menu switch 21.1) that is performed to activate a function included in the accompanying function group is invalidated.

At step S10 setting unit 2012 sets the unlock mode. More specifically, setting unit 2012 sets the accompanying function group in the activatable state (i.e., any operations can be performed).

Subsequently, activation controller 201 determines an instruction received from the user (step S12). More specifically, as has been described for step S6, it determines whether which switch of console 21 has been operated. If at step S12 a decision is made that measurement switch 21.3 has been pressed, measurement processing unit 203 performs the blood pressure measurement process (step S14). When step S14 completes, the process returns to step S12.

If at step S12 a decision is made that memory switch 21.6 has been pressed, measurement data display controlling unit 204 performs a process to display resultant measurement information on display 4 (step S15). When step S15 completes, the process returns to step S12.

If at step S12 a decision is made that menu switch 21.1 has been pressed and "erase measurement data" has been selected, then measurement data erasing unit 205 performs a process to erase resultant measurement information (step S16). When step S16 completes, the process returns to step S12.

Figure 5:
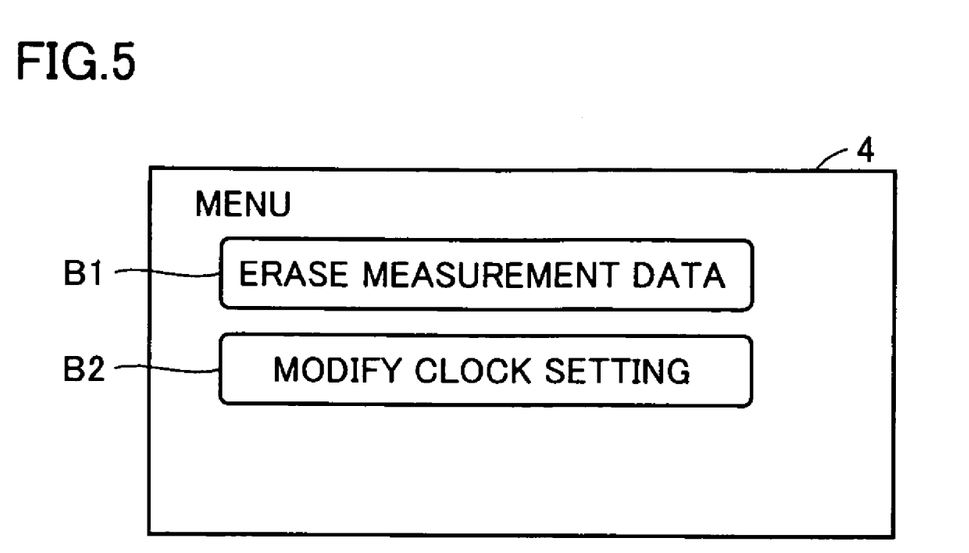
FIG. 5 shows an example of a screen displayed in an embodiment of the present invention when a menu switch is pressed.

When menu switch 21.1 is pressed, a screen is displayed by way of example as shown in FIG. 5. With reference to the figure, display 4 displays an item B1 corresponding to a measurement data erasure button and an item B2 corresponding to a clock-setting modification button. The measurement data erasure button or item B1 is an item for inputting an instruction to erase measurement data (or activate the erasure function) and the clock-setting modification button or item B2 is an item for inputting an instruction to modify a clock (or activate the value changing function). The user can press left switch 21.4 and right switch 21.5 to select any of the items and can press setting switch 21.2 to issue an instruction to activate a function corresponding to a currently selected item.

If at step S12 a decision is made that menu switch 21.2 has been pressed and "modify clock setting" has been selected, clock modifying unit 206 performs a process to modify a set time of timer 13 (step S17). When step S17 completes, the process returns to step S12.

Thus in the unlock mode operations of switches performed to activate any functions are validated.

Thus only when electronic blood pressure monitor 100 is started by a specific operation the accompanying function group can be set in the activatable state. This can prevent a subject from falsifying a measured value, a condition for measurement, and the like.

Exemplary Variation

In the above described embodiment a subject who does not know the specific operation cannot erase a measured value or change a set value. However, the subject may somehow obtain the specific operation. In that case the subject may falsify the measured value, the set value and the like. To address this, a history indicating that the electronic blood pressure monitor is started by the specific operation (hereinafter also referred to as a "history of the unlock start") may be stored to inform a supervisor of whether there is a possibility of falsification. Such electronic blood pressure monitor operates, as will be described hereinafter as an exemplary variation.

The exemplary variation provides an electronic blood pressure monitor having an external appearance and hardware configuration similar to electronic blood pressure monitor 100 described in the above embodiments. Accordingly, the reference characters indicated in FIGS. 1 and 2 will also be used hereinafter. Note that memory 12 and CPU 20 will in the exemplary variation be denoted as a memory 12A and a CPU 20A, respectively, as they are different in function (or control).

The exemplary variation differs from the above described embodiment, as described hereinafter.

Figure 6A:
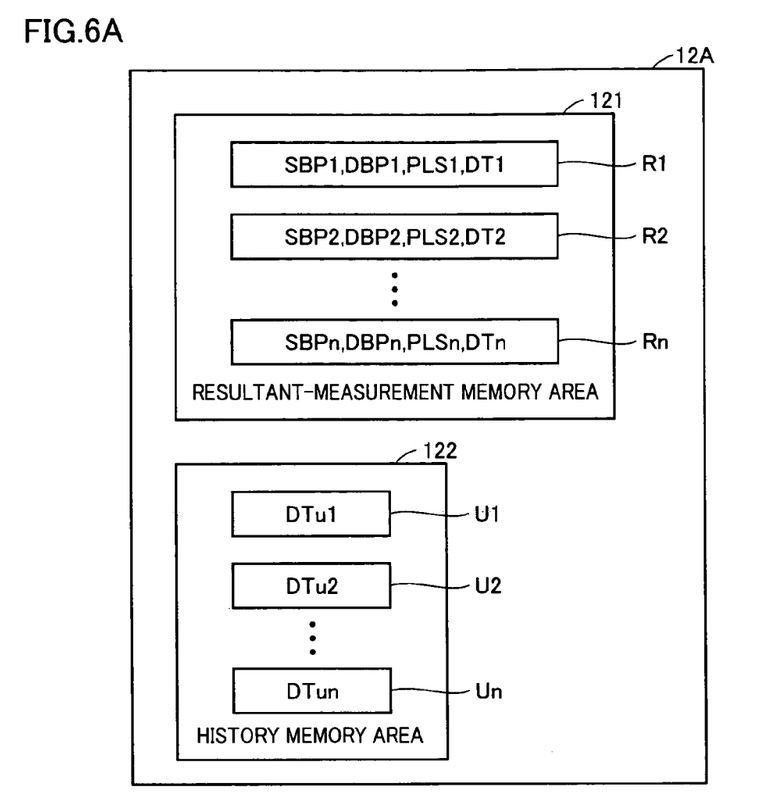
FIG. 6A shows an example in configuration of a memory in an exemplary variation of an embodiment of the present invention and FIG. 6B is a block diagram representing a function of a CPU in the present electronic blood pressure monitor in an exemplary variation of an embodiment.

FIG. 6A shows an example in configuration of memory 12A in the exemplary variation. In the exemplary variation memory 12A includes area 121 storing resultant measurement information, as described above, and in addition thereto an area 122 storing information of a history of the unlock start.

With reference to FIG. 6A, area 122 stores information specifying that electronic blood pressure monitor 100 has been started by the specific operation, e.g., start date and time data DTu. Area 122 is capable for example of storing a prescribed number of (e.g., five) start date and time data DTu and preferably has the oldest data overwritten with the latest data.

Figure 6B:
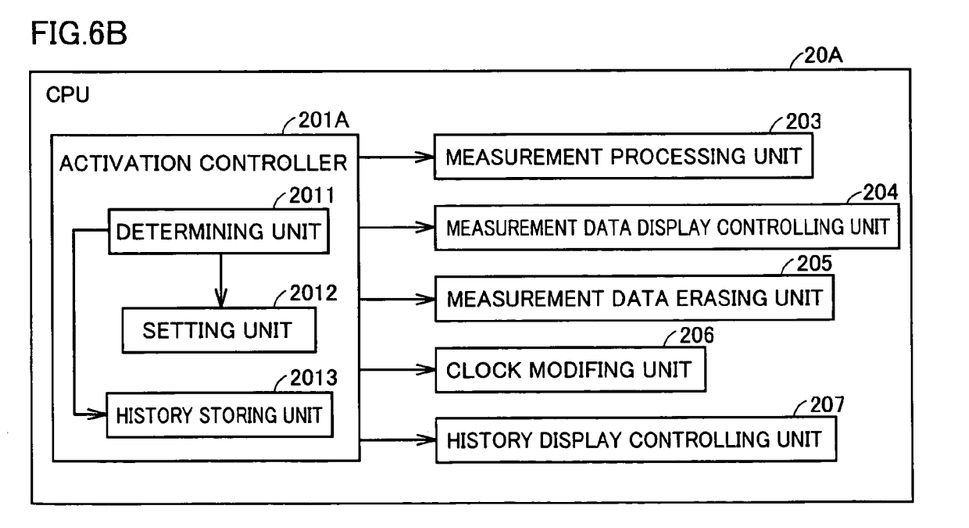

FIG. 6B is a block diagram representing a function of CPU 20A of electronic blood pressure monitor 100 in the present exemplary variation. With reference to the figure, as compared with the above described embodiment, activation controller 201A includes determining unit 2011 and setting unit 2012 and in addition thereto a history storing unit 2013. Furthermore CPU 20A further includes activation controller 201, measurement processing unit 203, measurement data display controlling unit 204, measurement data erasing unit 205 and clock modifying unit 206, and in addition thereto a history display controlling unit 207.

History storing unit 2013 stores data of a date and time of the unlock start to area 122 as start date and time data DTu.

History display controlling unit 207 reads start date and time data DTu from area 122 to perform a process to display it on display 4.

Note that in the exemplary variation a history display function is included in the accompanying function group for the sake of illustration. It should be noted, however, that this function is different from the information changing function and accordingly may be included in the basic function group.

Figure 7:
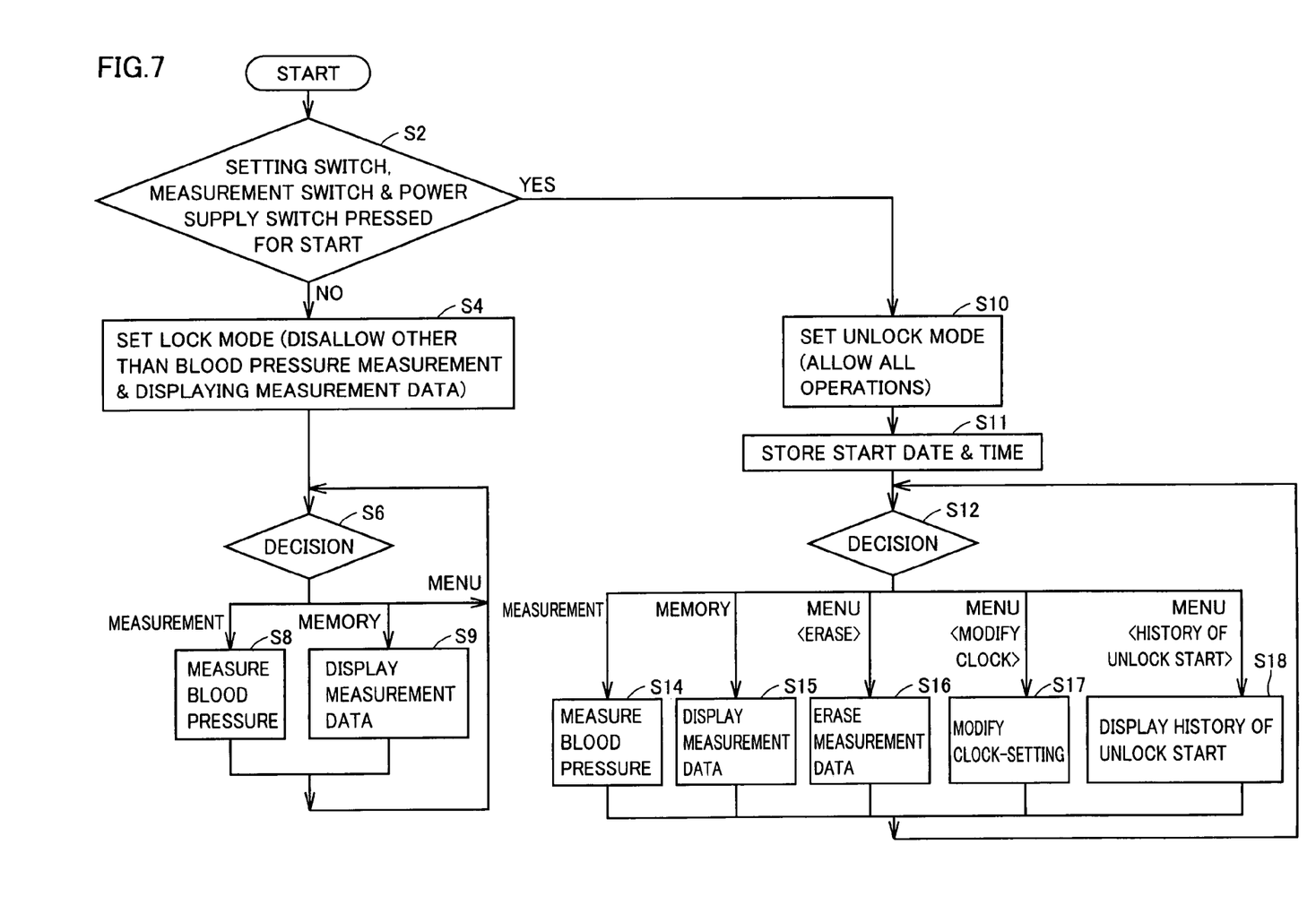
FIG. 7 is a flow chart of a process associated with measurement in an exemplary variation of an embodiment of the present invention.

FIG. 7 is a flow chart of a process associated with measurement, as provided in the present exemplary variation. The FIG. 7 flow chart also indicates a process previously stored in memory 12A as a program and implemented by CPU 20A reading and executing the program. Note that in the exemplary variation the process associated with measurement further includes a process performed by history display controlling unit 207 for the sake of illustration. Furthermore, steps similar to those of the FIG. 4 flow chart are identically labeled.

With reference to FIG. 7, in the exemplary variation between steps S10 and S12 a step (S11) is inserted to store start date and time. More specifically at step S11 history storing unit 2013 stores data of a date and time of the unlock start to area 122, as based on time count data provided from timer 13. Note that steps S10 and S11 may be performed vice versa.

Figure 8:
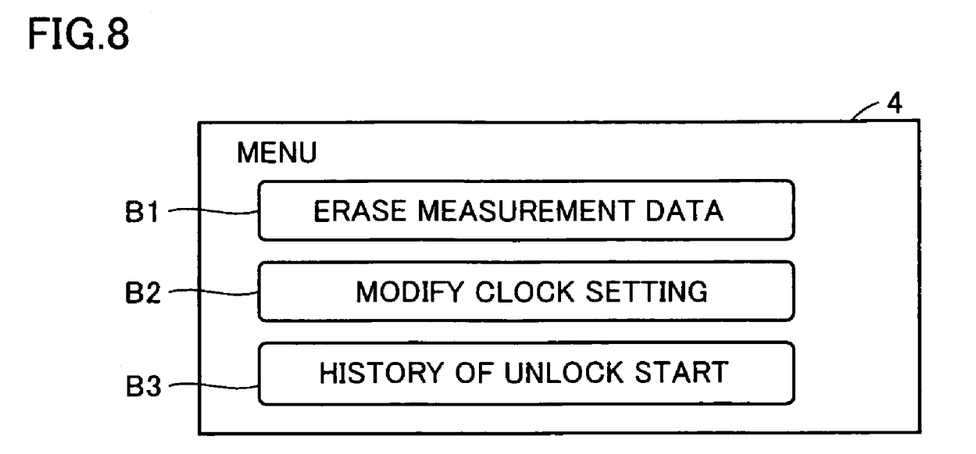
FIG. 8 shows an example of a screen displayed in an exemplary variation of an embodiment of the present invention when a menu switch is pressed.

In the exemplary variation at step S12 when menu switch 21.1 is pressed a screen is displayed by way of example as shown in FIG. 8. With reference to the figure, display 4 displays item B1 corresponding to the measurement data erasure button and item B2 corresponding to the clock-setting modification button, and in addition thereto an item B3 corresponding to a button pressed to input an instruction to display a history of the unlock start (or an instruction to activate the history display function).

Again with reference to FIG. 7 if at step S12 a decision is made that menu switch 21.1 has been pressed and the item B3 has been selected, history display controlling unit 207 performs a process to display a history of the unlock start (or date and time data DTu) on display 4 (step S18). When step S18 completes, the process returns to step S12.

Thus in the exemplary variation history information representative of a history of the unlock start can be confirmed and a supervisor can see whether there is a possibility of data falsification by a subject. Furthermore, neither the basic function group nor the accompanying function group includes a function erasing the history information, and whether the subject has started electronic blood pressure monitor 100 to operate in the unlock mode can reliably be stored.

Note that while as described herein the history information is described as information of a date and time of the unlock start, it is not limited thereto. For example, the history information may be information of how many times electronic blood pressure monitor 100 is started to operate in the unlock mode. In that case, history storing unit 2013 for example counts how many times electronic blood pressure monitor 100 is started within a prescribed period of time (e.g. of one week) to operate in the unlock mode, and stores the count's value to area 122.

Alternatively, the history information may include both information of a date and time at which the blood pressure monitor is started to operate in the unlock mode, and information of how many times it is done so. In that case, area 122 may store both start date and time data and count value data.

Furthermore, as described hereinabove, in the embodiment and its exemplary variation, the accompanying function group can be selected by pressing menu switch 21.1. However, switches assigned functions (the erasure function, the value changing function, the history display function), respectively, included in the accompanying function group, may further be provided at console 21. In that case, menu switch 21.1 may be dispensed with.

Alternatively, a common switch (e.g., menu switch 21.1) may be adapted to be operated to select the basic function group and the accompanying function group. In that case, measurement switch 21.3 and memory switch 21.6 can be dispensed with. For the unlock mode, when menu switch 21.1 is pressed, activation controller 201, 201A displays on display 4 a plurality of items (or first buttons) for allowing functions included in the basic function group to be all selectable, and an item (or a second button) for further displaying specifics of the accompanying function group. For the lock mode, when menu switch 21.1 is pressed, activation controller 201, 201A for example displays on display 4 the plurality of first buttons, and the second button in gray. Thus for the lock mode electronic blood pressure monitor 100 may be adapted to be unable to display a function included in the accompanying function group.

Furthermore the above described embodiment and its exemplary variation describes that electronic blood pressure monitor 100 is started to operate in the unlock mode by a specific operation simultaneously pressing a prescribed plurality of switches (including power supply switch 21.0) included in console 21. However, the specific operation is not limited thereto. For example, the blood pressure monitor's main body 1 may have at bottom surface (a surface opposite to that provided with display 4) or a similar portion hidden from external (or a location that the user can hardly find) a switch (not shown) dedicated to the unlock start. (Hereinafter this switch will be referred to as "the hidden switch.") In other words, the hidden switch is a switch operated to input an instruction to set the accompanying function group in the activatable state. In that case for example pressing power supply switch 21.0 and the hidden switch (not shown) simultaneously may correspond to the specific operation, or pressing the hidden switch (not shown) alone may correspond to the specific operation.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An electronic blood pressure monitor comprising:
   a blood pressure measurement unit for measuring blood pressure;
   a first storage for storing resultant measurement information including data of past measurements of said blood pressure measured by said blood pressure measurement unit and condition specifying data associated with each said blood pressure for specifying a condition while measuring said blood pressure;
   a display for displaying the resultant measurement information;
   a first input device operated to input an instruction to selectively activate a plurality of functions included in a first function group and a second function group of the electronic blood pressure monitor, said first function group including a measurement function provided by said blood pressure measurement unit and a first display function displaying on said display the resultant measurement information stored in said first storage, and said second function group including an erasure function erasing said resultant measurement information stored in said first storage and a value changing function changing a value serving as a reference for said condition for measurement, said first input device further including buttons to activate both the first function group and the second function group, said buttons available to a user regardless of whether or not the electronic blood monitor is started by a specific operation associated with the second function group;
   a timer for counting time, wherein said condition specifying data includes data of time counted by said timer when the blood pressure monitor measures said blood pressure; and
   an activation controller for exerting control in response to a signal representative of said instruction received via said first input device to selectively activate said plurality of functions, wherein said activation controller includes
      a determining unit for determining whether the electronic blood pressure monitor is started by said specific operation associated with said second function group,
      a setting unit driven by a decision made by said determining unit for setting said second function group in an activatable state or an inactivatable state, and
      wherein said activation controller selectively activates the function corresponding to said signal, the activated function being a function included in said first function group if said signal corresponds to said first function group or the activated function being a function included in said second function group if said signal corresponds to said second function group and said setting unit also sets said second function group in said activatable state.

2. The electronic blood pressure monitor according to claim 1, wherein said setting unit sets said second function group in said activatable state if said determining unit determines that the electronic blood pressure monitor is started by said specific operation, and said setting unit sets said second function group in said inactivatable state if said determining unit determines that the electronic blood pressure monitor is started by an operation other than said specific operation.

3. The electronic blood pressure monitor according to claim 1, further comprising a second storage for storing history information indicating that the electronic blood pressure monitor is started by said specific operation, wherein said second function group further includes a second display function displaying on said display said history information stored in said second storage.

4. The electronic blood pressure monitor according to claim 3, wherein said activation controller further includes a data storing unit for storing start date and time data as said history information to said second storage, as based on an output provided from said timer, when said determining unit determines that the electronic blood pressure monitor is started by said specific operation.

5. The electronic blood pressure monitor according to claim 3, wherein said activation controller further includes:
   a counter for counting how many times the electronic blood pressure monitor is started by said specific operation when said determining unit determines that the electronic blood pressure monitor is started by said specific operation; and
   a data storing unit for storing data of how many times the electronic blood pressure monitor is started by said specific operation, as counted, as said history information to said second storage.

6. The electronic blood pressure monitor according to claim 1, wherein said specific operation is included in power-on operations to start the electronic blood pressure monitor and is other than an explicit normal one of said power-on operations.

7. The electronic blood pressure monitor according to claim 6, wherein:
   said buttons include a plurality of switches capable of being pressed by the user; and
   said determining unit determines that the electronic blood pressure monitor is started by said specific operation when at least two prescribed ones of said plurality of switches are simultaneously pressed.

8. The electronic blood pressure monitor according to claim 6, further comprising a second input device hidden from external, wherein said determining unit determines that the electronic blood pressure monitor is started by said specific operation when said second input device is operated.

* * * * *